US008481043B2

(12) United States Patent
Bergenhem et al.

(10) Patent No.: US 8,481,043 B2
(45) Date of Patent: Jul. 9, 2013

(54) NASAL IMMUNIZATION

(75) Inventors: Nils Bergenhem, Guilford, CT (US); Lance Berman, Portsmouth, NH (US)

(73) Assignee: CPEX Pharmaceuticals, Inc., Exeter, NH (US)

( * ) Notice: Subject to any disclaimer, the term of this patent is extended or adjusted under 35 U.S.C. 154(b) by 314 days.

(21) Appl. No.: 12/794,629

(22) Filed: Jun. 4, 2010

(65) Prior Publication Data

US 2010/0278812 A1 Nov. 4, 2010

(51) Int. Cl.
*A61K 39/00* (2006.01)
*A61K 39/07* (2006.01)

(52) U.S. Cl.
USPC .................................... 424/184.1; 424/246.1

(58) Field of Classification Search
None
See application file for complete search history.

(56) References Cited

U.S. PATENT DOCUMENTS

| | | | |
|---|---|---|---|
| 3,915,921 | A | 10/1975 | Schlatzer, Jr. |
| 4,509,949 | A | 4/1985 | Huang et al. |
| 5,023,252 | A | 6/1991 | Hsieh |
| 5,591,631 | A | 1/1997 | Leppla |
| 5,677,274 | A | 10/1997 | Leppla |
| 5,731,303 | A | 3/1998 | Hsieh |
| 5,840,312 | A | 11/1998 | Mock et al. |
| 6,086,901 | A | 7/2000 | O'Hagan |
| 6,267,966 | B1 | 7/2001 | Baillie |
| 6,290,973 | B1 | 9/2001 | Hawkins |
| 6,316,006 | B1 | 11/2001 | Ivins et al. |
| 6,355,257 | B1 | 3/2002 | Johnson |
| 7,628,990 | B2 | 12/2009 | Tuck |
| 7,727,532 | B2 | 6/2010 | Thomas, Jr. |
| 2003/0003109 | A1 | 1/2003 | Galloway |
| 2004/0082530 | A1 | 4/2004 | Schmaljohn |
| 2004/0166120 | A1 | 8/2004 | Thomas |
| 2004/0197343 | A1 | 10/2004 | Dubensky, Jr. |
| 2005/0063986 | A1 | 3/2005 | Bhatnagar |
| 2007/0265191 | A1 | 11/2007 | Gyurik et al. |
| 2008/0063696 | A1 | 3/2008 | Glenn et al. |
| 2008/0317784 | A1 | 12/2008 | O'Hagan |
| 2009/0136480 | A1 | 5/2009 | Glenn et al. |
| 2009/0214596 | A1 | 8/2009 | Seino |
| 2009/0281522 | A1 | 11/2009 | Thio |
| 2009/0291894 | A1 | 11/2009 | Tezapsidis |
| 2009/0297556 | A1 | 12/2009 | Baillie |
| 2009/0317377 | A1 | 12/2009 | Yeomans |
| 2009/0326275 | A1 | 12/2009 | DiMauro |
| 2010/0003276 | A1 | 1/2010 | Hermes |
| 2010/0092526 | A1 | 4/2010 | Baker, Jr. |
| 2010/0278812 | A1 | 11/2010 | Bergenhen et al. |

FOREIGN PATENT DOCUMENTS

| | | |
|---|---|---|
| EP | 0689454 | 1/1996 |
| EP | 0761231 | 3/1997 |
| EP | 0835318 | 4/1998 |
| GB | 2220221 | 1/1990 |
| WO | WO90/14837 | 12/1990 |
| WO | WO92/19265 | 11/1992 |
| WO | WO93/13202 | 7/1993 |
| WO | WO98/57659 | 12/1998 |
| WO | WO99/11241 | 3/1999 |
| WO | WO99/52549 | 10/1999 |
| WO | WO00/07621 | 2/2000 |
| WO | WO00/23105 | 4/2000 |
| WO | WO00/56358 | 9/2000 |
| WO | WO00/62800 | 10/2000 |
| WO | WO01/21152 | 3/2001 |
| WO | WO01/21207 | 3/2001 |

OTHER PUBLICATIONS

Basu, et al. "Development and Evaluation of a Mucoadhesive Nasal Gel of Midazolam Prepared with *Linam usitatissimum* L. Seed Mucilage," Scientia Pharmaceutica. 2009, vol. 77; pp. 899-910.
CDC. Morbidity and Mortality Weekly Report [online]. Retrieved from the Internet <http://www.cdc.gov/mmwr/PDF/rr/rr4608.pdf> Apr. 4, 1997.
Wikipedia [online]. Retrieved from the Internet <http://en.wikipedia.org/wiki/Passive_immunity> May 16, 2010.
CDC [online]. Retrieved from the Internet <http://www.cdc.gov/vaccines/recs/provisional/downloads/pneumo-Oct-2008-508.pdf> Dec. 8, 2008.
Amgen Inc. [online] Retrieved from the Internet <http://pi.amgen.com/united_states/prolia/prolia_pi.pdf> Jun. 2010.
ATCC [online] Retrieved from the Internet <http://www.atcc.org/culturesandproducts/microbiology/purifiedpneumococcalpolysaccharides/tabid/185/default.aspx> May 27, 2010.
Skountzou, et al. "Transcutaneous immunization with inactivated influenza virus induces protective immune responses," Vaccine. May 26, 2006, vol. 24; pp. 6110-6119.
Moredun Research Institute [online]. Retrieved from the Internet <http://www.mri.sari.ac.uk/pdf/bact-jclark-poster1.pdf>.
Güereña-Burgueño, et al. "Safety and Immunogenicity of a Prototype Enterotoxigenic *Escherichia coli* Vaccine Administered Transcutaneously," Infection and Immunity. Apr. 2002, pp. 1874-1880.
Widman, et al. "Construction and characterization of a second-generation pseudoinfectious West Nile virus vaccine propagated using a new cultivation system," Vaccine. 2008, vol. 26; pp. 2762-2771.
Flick-Smith, et al. "Mucosal or Parenteral Administration of Microsphere-Associated *Bacillus anthracis* Protective Antigen Protects against Anthrax Infection in Mice," Infection and Immunity. Apr. 2002, vol. 70; pp. 2022-2028.
Gaur, et al. "Effect of nasal immunization with protective antigen *Bacillus anthracis* on protective immune response against anthrax toxin," Vaccine. Jun. 21, 2002, vol. 20; pp. 2836-2839.
Boyaka, et al. "Effective Mucosal Immunity to Anthrax: Neutralizing Antibodies and Th Cell Responses Following Nasal Immunization with Protective Antigen," The Journal of Immunology. 2003, vol. 170; pp. 5636-5643.

(Continued)

*Primary Examiner* — Jeffrey E Russel
(74) *Attorney, Agent, or Firm* — Ohlandt, Greeley, Ruggiero & Perle, LLP

(57) ABSTRACT

Compositions and methods for intranasal delivery of antigens for immunization of a mammal are disclosed. Antigens include peptides, proteins, peptidomimetics, DNA, RNA, carbohydrates and phospholipids. The compositions contain at least one antigen and a permeation enhancer. The permeation enhancer can be a macrocyclic permeation enhancer, such as a Hsieh enhancer.

11 Claims, No Drawings

OTHER PUBLICATIONS

Milich, et al. "Conversion of poorly immunogenic malaria repeat sequences into a highly immunogenic vaccine candidate," Vaccine. Dec. 12, 2001, vol. 20; Issues 5-6, pp. 771-788.
Coulson, et al. "*Bacillus anthracis* protective antigen, expressed in *Salmonella typhimurium* SL 3261, affords protection against anthrax spore challenge," Vaccine. 1994, vol. 12; Issue 15, pp. 1395-1401.
Garmory, et al. "*Salmonella enterica* serovar Typhimurium expressing a chromosomally integrated copy of the *Bacillus anthracis* protective antigen gene protects mice against an anthrax spore challenge," Infection and Immunity. Jul. 2003, vol. 71; Issue 7, pp. 3831-3836.
Aloni-Grinstein, et al. "Oral spore vaccine based on live attenuated nontoxinogenic *Bacillus anthracis* expressing recombinant mutant protective antigen," Infection and Immunity. Jul. 2005, vol. 73, Issue 7, pp. 4043-4053.
Vodkin, et al. "Cloning of the protective antigen gene of *Bacillus anthracis*," Cell. Sep. 1983, vol. 34, pp. 693-697.
Ivins, et al. "Cloning and expression of the *Bacillus anthracis* protective antigen gene in *Bacillus subtilis*," Infection and Immunity. Nov. 1986, vol. 54, Issue 2, pp. 537-542.
Baillie, et al. "Evaluation of *Bacillus subtilis* strain IS53 for the production of *Bacillus anthracis* protective antigen," Letters in Applied Microbiology. 1994, vol. 19, Issue 4, pp. 225-227.
Welkos, et al. "Sequence analysis of the DNA encoding protective antigen of *Bacillus anthracis*," Gene. 1988, vol. 69, pp. 287-300.
Fornadley. "Allergy Immunotherapy," Otolaryngologic Clinics North America. 1988, vol. 31, pp. 111-127.
Johnson, D.A., et al. "Synthesis and biological evaluation of a new class of vaccine adjuvants: aminoalkyl glucosaminide 4-phospates (AGPs)," Bioorganic & Medicinal Chemistry Letters. Aug. 2, 1999, vol. 9, Issue 15, pp. 2273-2278.
Vasilakos, J.P., et al. "Adjuvant activities of immune response modifier R-848: comparison with CpG ODN," Cellular Immunology. Aug. 25, 2000, vol. 204, Issue 1, pp. 64-74.
Hawkins, L.D., et al. "A novel class of endotoxin receptor agonists with simplified structure, toll-like receptor 4-dependent immunostimulatory action, and adjuvant activity," Journal of Pharmacology and Experimental Therapeutics. Feb. 2002, vol. 300, Issue 2, pp. 655-661.
Raz, E., et al. "Intradermal gene immunization: the possible role of DNA uptake in the induction of cellular immunity to viruses," Proceedings of the National Academy of Sciences. Sep. 1994, vol. 91, pp. 9519-9523.
Little, S.F., et al. "Production and characterization of monoclonal antibodies against the lethal factor component of *Bacillus anthracis* lethal toxin," Infection and Immunity. Jun. 1990, vol. 58, Issue 6, pp. 1606-1613.
Pitt, M.L.M., et al. "Invitro correlate of immunity in a rabbit model of inhalational anthrax," Vaccine. 2001, vol. 19, pp. 4768-4773.
Wenneras, C., et al. "Antibody-secreting cells in human peripheral blood after oral immunization with an inactivated enterotoxigenic *Escherichia coli* vaccine," Infection and Immunity. Jul. 1992, vol. 60, Issue 7, pp. 2605-2611.
Jertborn, M., et al. "Dose-Dependent Circulating Immunoglobin A Antibody-Secreting Cell and Serum Antibody Responses in Swedish Volunteers to an Oral Inactivated Enterotoxigenic *Escherichia coli* Vaccine," Clinical and Diagnostic Laboratory Immunology. Mar. 2001, vol. 8, pp. 424-428.
Jertborn, M., et al. "Safety and immunogenicity of an oral inactivated enterotoxigenic *Escherichia coli* vaccine," Vaccine. 1998, vol. 16, pp. 255-260.
Lo-Man, R., et al. "A Fully Synthetic Therapeutic Vaccine Candidate Targeting Carcinoma-Associated Tn Carbohydrate Antigen Induces Tumor-Specific Antibodies in Nonhuman Primates," Cancer Research. Jul. 15, 2004, vol. 64, pp. 4987-4994.
Duffy, M.J., et al. "CA 19-9 as a marker for gastrointestinal cancers: a review," Annals of Clinical Biochemistry. 1998, vol. 35, pp. 364-370.
Hermanson, G., et al. "A cationic lipid-formulated plasmid DNA vaccine confers sustained antibody-mediated protection against aerosolized anthrax spores," PNAS. 2004, vol. 101, Issue 37, pp. 13601-13606.
Clark, J.R., et al. "Bacterial viruses as human vaccines?," Expert Review of Vaccines. Aug. 2004, vol. 3, Issue 4, pp. 463-476.
March, J.B., et al. "Genetic immunisation against hepatitis B using whole bacteriophage lambda particles," Vaccine. Apr. 16, 2004, vol. 22 (13-14), pp. 1666-1671.
Clark, Jason R., et al. "Bacteriophage-mediated nucleic acid immunisation," FEMS Immunology & Medical Microbiology. Jan. 15, 2004, vol. 40, Issue 1, pp. 21-26.
Jepson, C.D., et al. "Bacteriophage lambda is a highly stable DNA vaccine delivery vehicle," Vaccine. Jun. 23, 2004, vol. 22, Issue 19, pp. 2413-2419.
Compans, R.W. "Hemagglutination-Inhibition: Rapid Assay for Neuraminic Acid-Containing Viruses," Journal of Virology. Nov. 1974, vol. 14, Issue 5, pp. 1307-1309.
Novak, M., et al. "Murine model for evaluation of protective immunity to influenza virus," Vaccine. 1993, vol. 11, Issue 1, pp. 55-60.
Sha, Z., et al. "Induction of CD4(+) T-Cell-Independent Immunoglobulin Responses by Inactivated Influenza Virus," Journal of Virology. Jun. 2000, vol. 74, Issue 11, pp. 4999-5005.
Kang, S.M. et al. "Enhancement of Mucosal Immunization with Virus-Like Particles of Simian Immunodeficiency Virus," Journal of Virology. Mar. 2003, vol. 77, Issue 6, pp. 3615-3623.
Kang, S.M., et al. "Intranasal Immunization with Inactivated Influenza Virus Enhances Immune Responses to Coadministered Simian-Human Immunodeficiency Virus-Like Particle Antigens," Journal of Virology. Sep. 2004, vol. 78, Issue 18, pp. 9624-9632.
Mason, P.W., et al. "Production and characterization of vaccines based on flaviviruses defective in replication," Virology. Aug. 1, 2006, vol. 351, Issue 2, pp. 432-443.
Xiao, S.Y. et al. "West Nile virus infection in the golden hamster (*Mesocricetus auratus*): a model for West Nile encephalitis," Emerging Infectious Diseases Journal. 2001, vol. 7, Issue 4, pp. 714-721.
Raney, Sam, et al. "30th anniversary of the Franz cell finite dose model: the crystal ball of topical drug development," Drug Delivery Technology. 2008, vol. 8, Issue 7, p. 32.
Schmidt, M.C., et al. "Validation of excised bovine nasal mucosa as in vitro model to study drug transport and metabolic pathways in nasal epithelium," Journal of Pharmaceutical Sciences. Mar. 2000, vol. 89, Issue 3, pp. 396-407.
International Search Report in PCT/US2011/39007 dated Nov. 25, 2011.
Written Opinion in PCT/US2011/39007 dated Nov. 25, 2011.
International Preliminary Report on Patentability dated Dec. 4, 2012 corresponding to International Patent Application No. PCT/US2011/039007.

SEQUENCE LISTING

```
<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic construct

<400> SEQUENCE: 1
tccatgacgt tcctgacgtt                                                  20
```

NASAL IMMUNIZATION

FIELD OF THE INVENTION

The present invention relates to compositions and methods for the delivery of antigens through the nasal mucosa for immunization of a mammal. Antigens include, peptides, proteins, peptidomimetics, DNA, RNA, carbohydrates and phospholipids.

BACKGROUND OF THE INVENTION

Injection is the most commonly used method for administering vaccines and protein therapeutics, such as insulin, to humans. However, injection therapies have numerous drawbacks such as discomfort to the patient, poor patient compliance, and the need for administration by trained technicians.

A desired alternative method of immunization would be intranasal administration of a composition containing a therapeutically effective amount of an antigen. The intranasal route may be suited to mass vaccination, given the simplicity of the delivery systems, their ease of use, and minimal invasiveness. Many pathogens infect via the respiratory mucosa; therefore, immunization at these mucosal sites can be more efficacious than immunization by injection.

However, intranasal delivery of antigens, many of them being macromolecules such as peptides or proteins, have had limited success because the antigens are not particularly effective in penetrating the mucous membrane of the nasal passage, and because the tendency of some permeation agents to irritate those membranes.

Anthrax is an infection caused by the spore-forming bacterium *Bacillus anthracis*. Anthrax may enter the body and cause infection by means of inhalation, ingestion or subcutaneous exposure. Recent heightened awareness of the possibility of bioterrorism has raised concerns about the use of *B. anthracis* or related strains, both newly emerging or genetically engineered, as bio-weapons. Anthrax protective antigen (PA) has been administered intranasally as a liquid in mice and has provided protection against aerosol challenge in murine models. Flick-Smith et al. Mucosal or parenteral administration of microsphere-associated *Bacillus anthracis* protective antigen protects against anthrax infection in mice. *Infect. Immun.* 2002; 70:2022-8. Gaur et al. Effect of nasal immunization with protective antigen of *Bacillus anthracis* on protective immune response against anthrax toxin. *Vaccine* 2002; 20: 2836-9. Boyaka et al. Effective mucosal immunity to anthrax: neutralizing antibodies and Th cell responses following nasal immunization with protective antigen. *J. Immunol.* 2003; 170: 5636-43.

There still remains a need for an effective and safe vaccine that would effectively produce immunity to anthrax with fewer doses.

By using permeation enhancers, the present invention provides compositions and methods for efficient nasal immunization against various antigens, including anthrax. The ability to confer protection following intranasal delivery is particularly attractive in the context of a bioterrorism event as it would greatly simplify the process of mass vaccinations. The present invention includes within its scope also the intranasal method of delivering peptides, peptidomimetics and proteins in general for therapeutic purposes.

SUMMARY OF THE INVENTION

The present invention provides for a pharmaceutical composition for nasal immunization comprising: a macrocyclic permeation enhancer, a liquid carrier, an emulsifying agent, and a therapeutically effective amount of an antigen; wherein said macrocyclic permeation enhancer is a Hsieh enhancer. The Hsieh enhancer may be 3-methylcyclopentadecanone, 9-cycloheptadecen-1-one, cyclohexadecanone, cyclopentadecanone, oxacyclohexadecan-2-one or mixtures thereof. The antigen may be a protein or peptide (such as the Anthrax protective antigen), a carbohydrate or DNA. The composition may further comprise a crystallization inhibitor, and/or an enzyme inhibitor such as leupeptin and aprotinin.

The present invention further provides for method of immunizing a mammal comprising the steps of: (a) formulating a composition comprising: a macrocyclic permeation enhancer, a liquid carrier, an emulsifying agent, and a therapeutically effective amount of an antigen; wherein said macrocyclic permeation enhancer is a Hsieh enhancer, and (b) administering the composition to the mammal by nasal administration.

Also encompassed by the present invention is a pharmaceutical composition for nasal immunization comprising: a macrocyclic permeation enhancer, a liquid carrier, an emulsifying agent, and a therapeutically effective amount of an antibody; wherein said macrocyclic permeation enhancer is a Hsieh enhancer.

DETAILED DESCRIPTION OF THE INVENTION

The present invention provides a pharmaceutical composition for nasal immunization which is capable of inducing an effective immune response. The pharmaceutical composition is in a form suitable for intranasal delivery and contains a therapeutically effective amount of an antigen and a permeation enhancer. Antigens that may be used with the compositions and methods of the present invention can be any agent that generates an immune response, e.g., humoral (antibody) responses and/or cellular immune response. Antigens may be an allergen or a microorganism (or a part of a microorganism). The preparation of a particular immunizing formulation and the protocol will depend on the type of antigen to be used; however, the development of both the formulation and the protocol is well within the scope of one of ordinary skill in the art. The pharmaceutical composition also encompassed by the present invention is in a form suitable for intranasal delivery and contains a therapeutically effective amount of an antibody and a permeation enhancer.

Antigens that may be used in the present compositions include, but are not limited to, proteins, peptides, peptidomimetics (synthetic peptides), carbohydrates (including monosaccharides, disaccharides, oligosaccharides and polysaccharides), lipids, nucleic acids (e.g., DNA and RNA), and conjugates/mixtures thereof. Nucleic acid antigens includes a DNA or RNA fragment, a DNA fragment incorporated into a vector such as a plasmid, ribozyme, antisense oligonucleotide, siRNA and shRNA. Examples of polynucleotide-containing antigens include, for example, (a) nucleic acid sequences that directly encode polypeptide-containing antigens (e.g., mRNA molecules) and (b) vector constructs that indirectly encode polypeptide-containing antigens, for example, vector constructs that express heterologous nucleic acid sequences, which in turn encode polypeptide-containing antigens (e.g., DNA vector constructs and RNA vector constructs). The antigen can be parts (e.g., coats, capsules, cell walls, flagella, fimbrae, and toxins) of microorganisms. The antigen can also be attenuated live microorganism or inactivated microorganisms. The microorganisms include, but are not limited to, viruses (e.g., influenza virus, avian influenza virus, parainfluenza virus, adenovirus, SARS virus, AIDS virus, cytomegalovirus, hepatitis virus, Japanese encephalitis virus, measles virus and the like), bacteria (e.g., *Bacillus anthracis, Streptococcus pneumoniae, Neisseria meningitidis, Staphylococcus, Pseudomonas aeruginosa* and the like), fungi (e.g., *Cryptococcus, Aspergillus* and the like), protozoan (e.g., malaria and the like), other microorganisms and toxin, cadaver of insect (e.g., mite and the like), pollen and the like. The antigen usable for the composition of the present invention is not particularly limited as long as it affords an effective immune response. In certain embodiments, the immune response includes an increase in the intranasal IgA antibody titer and an increase in the blood IgG antibody titer, as well as to be protective against the antigen or the microorganism in the vaccinated subject.

A peptide is a protein fragment comprising a short chain of amino acids, no less than two amino acids. A protein is generally a longer chain of amino acids, though there is no exact rule as to where a peptide ends and a protein begins. The general peptide/protein nomenclature also considers whether the structure is a whole molecule, such as insulin-like growth factor-1 (IGF-1) that is a 73 amino acids long peptide, or if the structure is a fragment of a protein molecule, such as a trypsin cleaved fragment of a protein that would normally be called a tryptic peptide.

In general, the peptides, peptidomimetics, and proteins used in the present invention have molecular weights on the order of about 150 to about 200,000 daltons, about 1,000 to about 180,000 daltons, about 2,000 to about 150,000 daltons, about 3,000 to about 100,000 daltons, about 50,000 to about 100,000 daltons, about 20,000 to about 50,000 daltons, or about 30,000 to about 50,000 daltons. In one embodiment the peptides used in the present invention have molecular weights on the order of about 150 to about 30,000 daltons, though other peptides, which, due to their tertiary or quaternary structure may be larger than 30,000 daltons, are also within the scope of the invention. In certain embodiments, the peptides used in the present invention have molecular weights on the order of about 150 to about 10,000 daltons, or about 150 to about 7,000 daltons.

Proteins and peptides may be generated by recombinant techniques. Thus, chimeric molecules containing regions from different proteins may be used. For example, a recombinant protein containing the *Plasmodium falciparum* malaria circumsporozoite repeat region fused to a section of the Hepatitis B core antigen may be used. Milich et al., Conversion of poorly immunogenic malaria repeat sequences into a highly immunogenic vaccine candidate, *Vaccine*, Volume 20, Issues 5-6, (2001) Pages 771-788.

The compositions of the present invention may be used for immunization against one or more than one type of microorganism or allergen. The compositions may contain one type of antigen or more than one type of antigen.

The composition of the present invention can be used for immunization against anthrax. The infective process of anthrax is as follows. It occurs when the spores are taken up by the body, through inhalation, ingestion or subcutaneous exposure. The spores become active toxic bacteria and express anthrax toxin, which will ultimately halt the host's immune response and cause cell death. Anthrax toxin has three components: anthrax protective antigen (PA), anthrax edema factor (EF) and anthrax lethal factor (LF). PA binds an anthrax toxin receptor (ATR) on the surface of the host cell. PA is then cleaved by a host protease, activating PA, which then binds to other active PAs to form a heptamer. The heptamer then binds EF or LF and the entire complex is drawn into the cell via endocytosis, forming an endosome within the host cell. EF or LF is ejected from the endosome, into the cytosol of the cell. Once in the cytosol, LF and EF exert their enzymatic activities, interrupt cell signaling and damage the cells. EF ultimately causes edema and LF ultimately causes cell lysis.

Antigens for use against anthrax in the present invention can be derived from a variety of *Bacillus anthracis* strains, and can include killed, attenuated or inactivated *Bacillus anthracis* as well as subunit antigens. The antigens include protein containing species, peptide containing species (e.g., protective antigen (PA), polysaccharide containing species, and polynucleotide containing species which express an immunogenic protein or polypeptide.

Anthrax antigens include protective antigen (PA) based antigens, e.g., purified protein from *B. anthracis* culture or live-attenuated spore vaccine antitoxin vaccines, such as AVA (Anthrax Vaccine Adsorbed, commercially available from Emergent Biosolutions of Gaithersburg, Md. (formerly Bioport Corporation, Lansing, Mich.)) or any of the more modern, defined PA, capsule-based or a conjugate of PA and capsule-based vaccines. AVA consists of a membrane-sterilized culture filtrate of *B. anthracis* V770-NP1-R, an avirulent, nonencapsulated strain. The culture filtrate is adsorbed to aluminum hydroxide and formulated with benzethonium chloride (preservative) and formaldehyde (stabilizer). Any type of anthrax toxin or capsule antigens may be used. U.S. Patent Publication Nos. 20100003276, 20090297556, 20080317784. Various vaccines have been discussed that target the natural mechanism of PA, LF and/or EF. For example, U.S. Pat. Nos. 5,591,631 and 5,677,274 describe fusion proteins including domains of PA and/or LF. In another approach, U.S. Patent Application No. 2004/0166120 has described a composition which contains PA and a truncated, non-functional *B. anthracis* LFn for eliciting a *B. anthracis* immune response. Additionally, U.S. Patent Application No. 2003/0003109 discusses vaccines that administer a polynucleotide with a coding sequence for a mutated LF protein or an immunogenic fragment of an LF protein and a polynucleotide with a coding sequence for PA or an immunogenic fragment of PA to a subject. U.S. Patent Application No. 2005/0063986 discusses recombinant DNA constructs containing wild type or mutant type PA, LF or EF. Additional approaches have focused on live vaccines as expression systems for PA, LF or EF. Specific attempts also focused on use of live *Salmonella* and *B. anthracis*. Coulson, et al. *Vaccine*, vol. 12, No. 15, 1395-1401 (1994). Garmory, et al. *Infect. Immun.*, 71(7): 3831-6 (2003). Aloni-Grinstein, et al. *Infect. Immun.*, 73(7): 4043-53 (2005). Additional work has focused on the possibilities of development of live vaccines. U.S. Application No. 2004/0197343. Moreover, a number of alternative procaryotic (bacterial) expression systems have been developed for antigen production, including an *Escherichia coli* expression system (Vodkin et al. (1983) Cell 34:693-697), a *Salmonella typhimurium* expression system (Coulson et al. (1994) Vaccine 12:1395-1401), a *Bacillus subtilis* expression systems (see, e.g., U.S. Pat. No. 6,267,966 to Baillie; Ivins et al. (1986) Infection and Immunity 54:537-542; and Baillie et al. (1994) Let. Appl. Microbiol. 19:225-227), and a number of recombinant *Bacillus anthracis* expression systems that are either asporogenic or unable to produce the LF or EF toxins (see, e.g., U.S. Pat. No. 5,840,312 to Mock et al. and U.S. Pat. No. 6,316,006 to Worsham et al.). Moreover, the complete gene sequence for the *B. anthracis* PA antigen is known (Welkos et al. (1988) Gene 69:287-300) and publicly available, enabling the development and production of a wide variety of antigens, including polypeptide containing and polynucleotide containing antigens. For example, U.S. Patent Application 2004/0082530 describes nucleic acids that contain sequences encoding polypeptide antigens obtained or derived from *B. anthracis*, including sequences encoding the PA antigen and sequences encoding other antigens such as fragments of the EF or LF antigens, which can be inserted into appropriate vector constructs using known techniques.

The antigen is present in the composition in a therapeutically effective amount. In general the antigen is present in an amount of about 0.001 to about 50 wt. % of the composition, about 0.01 to about 30 wt. %, about 0.1 to about 20 wt. %, about 0.1 to about 10 wt. %, or about 0.1 to about 2 wt. % of the composition.

The antigen of the present invention may be used in a comparatively crude state, or may be purified before use. For purification, for example, a method conventionally used in the art for the purification of a peptide, protein, DNA, RNA, carbohydrate, may be carried out in the present invention, such as filtration, concentration, centrifugation, gel filtration chromatography, ion exchange chromatography, hydrophobic chromatography, adsorption chromatography, high performance liquid chromatography, affinity chromatography, gel electrophoresis, isoelectric focusing and the like. When necessary, these methods may be combined as appropriate. According to the form of final use, purified antigen may be concentrated or freeze-dried to give a liquid or solid.

The pharmaceutical compositions of the present invention may also be used in desensitization. For example, increasing doses of an allergen are administered to a subject who has demonstrated sensitivity to the allergen. Examples of allergen doses used for desensitization are known in the art, see, for example, Formadley (1998) Otolaryngol. Clin. North Am. 31:111-127.

At least one immunological adjuvant may be used in the present composition to assist or modify the action of an antigen. Immunological adjuvants may lead to one or more of the following effects, among others: an increased immune response, a more diversified immune response, an accelerated immune response, a more persistent/prolonged immune response. Adjuvants that may be used in the present invention include, but are not limited to, dextran or cyclodextran and saponin, Polynucleotide-containing immunological adjuvants (e.g., DNA- and/or RNA-containing immunological adjuvants, such as oligodeoxynucleotides and double-stranded RNA), and polymer microparticles.

Non-limiting examples of adjuvants include: (1) aluminum salts (alum), such as aluminum hydroxide, aluminum phosphate, aluminum sulfate, etc.; (2) submicron emulsions comprising a metabolizable oil, such as squalene, and an emulsifying agent, such as one or more sorbitan derivatives, for example, (a) MF59 (International Publication No. WO90/14837; Chapter 10 in Vaccine design: the subunit an adjuvant approach, Eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribij adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DetoxJ) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., Stimulonj (Cambridge Bioscience, Worcester, Mass.)) may be used or particles generated therefrom such as ISCOMs (immunostimulating complexes), which ICOMS may be devoid of additional detergent e.g., WO00/07621; (4) Complete Freunds Adjuvant (CFA) and Incomplete Freunds Adjuvant (IFA); (5) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (6) phospholipid adjuvants, including lipopolysaccharide and liposaccharide phosphate adjuvants, for example, monophosphoryl lipid A (MPL) and its derivatives, 3-O-deacylated MPL (3dMPL) e.g. GB-2220221, EP-A-0689454, optionally in the substantial absence of alum when used with pneumococcal saccharides e.g. WO00/56358; as well as aminoalkyl glucosamine phosphate compounds such as those described in U.S. Pat. No. 6,355,257; (7) combinations of 3dMPL with, for example, QS21 and/or oil-in-water emulsions, e.g., EP-A-0835318, EP-A-0735898, EP-A-0761231; (8) a polyoxyethylene ether or a polyoxyethylene ester e.g. WO99/52549; (9) a polyoxyethylene sorbitan ester surfactant in combination with an octoxynol (WO01/21207) or a polyoxyethylene alkyl ether or ester surfactant in combination with at least one additional non-ionic surfactant such as an octoxynol (WO01/21152); (10) a saponin and an immunostimulatory oligonucleotide (e.g., a CpG oligonucleotide) (WO00/62800); (11) an immunostimulant and a particle of metal salt e.g. WO00/23105; (12) a saponin and an oil-in-water emulsion e.g. WO99/11241; (13) a saponin (e.g. QS21)+3dMPL+IL-12 (optionally+a sterol) e.g. WO98/57659; (14) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (15) aminoalkyl glucosaminide 4-phosphates (AGP's), see, e.g., Johnson, D. A. et al.; Bioorg. Med. Chem. Lett., 1999 Aug. 2; 9(15):2273-8, (16) imidazoquinolines such as imiquimod (R-837) and resiquimod (R-848), see, e.g., Vasilakos, J. P. et al.; Cell. Immunol. 2000 Aug. 25; 204(1):64-74, (17) lipopolysaccharide mimetics (including monophosphoryl lipid A mimetics), such as non-saccharide phospholipids (e.g., simplified lipid A analogs lacking a disaccharide) described in Hawkins, L. D. et al; J. Pharmacol. Exp. Ther., 2002 February; 300(2):655-61 and U.S. Pat. No. 6,290,973; and (18) other substances that act as immunostimulating agents to enhance the effectiveness of the composition. Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-s-n-glycero-3-huydroxyphosphoryloxy)-ethylamine (MTP-PE), etc. U.S. Patent Publication Nos. 20080317784, 20090214596 and 20100092526.

For additional examples of immunological adjuvants, see *Vaccine Design, The Subunit and the Adjuvant Approach*, Powell, M. F. and Newman, M. J, eds., Plenum Press, 1995.

The pharmaceutical composition also encompassed by the present invention contains a therapeutically effective amount of an antibody and a permeation enhancer. In certain embodiments, the pharmaceutical compositions and methods of the present invention may be used for passive immunization. See, for example, en.wikipedia.org/wiki/Passive immunity.

The antibodies of the present composition may contain one or more polypeptides. The antibodies may be an intact antibody, or an antibody fragment (e.g., Fab, nanobodies). Monoclonal antibodies, polyclonal antibodies, or mixture thereof can be used in accordance with the present invention. The antibodies may be types IgA, IgG, IgE, IgD or IgM (as well as subtypes thereof), wherein the light chains of the immunoglobulin may be of types kappa or lambda. The complementarity determining regions (CDRs) of the antibodies can be from a human or non-human source. The framework of the antibodies can be human, humanized, or non-human, e.g., a murine framework modified to decrease antigenicity in humans, or a synthetic framework, e.g., a consensus sequence.

Antibodies may be obtained, isolated or purified from an animal including human, or may be prepared, expressed, created, or isolated by recombinant means. For example, antibodies can be expressed using a recombinant expression vector transfected into a host cell, isolated from a recombinant, combinatorial antibody library, isolated from an animal (e.g., a mouse) that is transgenic for human immunoglobulin genes, or prepared, expressed, created, or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences. U.S. Pat. No. 7,727,532.

In general, the permeation enhancer that is employed is one that enhances the permeation of an antigen through the nasal mucosa. The general formula of the permeation enhancer is shown below.

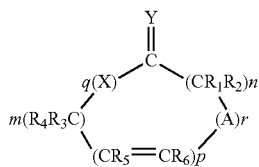

wherein X and Y are oxygen, sulfur or an imino group of the structure

or =N—R with the proviso that when Y is the imino group, X is an imino group, and when Y is sulfur, X is sulfur or an imino group, A is a group having the structure

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, and said compound will enhance the rate of the passage of an antigen (or an antibody) across body membranes. Hereinafter these compounds are referred to as enhancers. When R, $R_1$, $R_2$, $R_3$, $R_4$, $R_5$ or $R_6$ is alkyl it may be methyl, ethyl, propyl, isopropyl, butyl, isobutyl, sec-butyl, amyl, hexyl, and the like. Such permeation enhancers are described in U.S. Pat. Nos. 5,023,252 and 5,731,303.

Preferably, the permeation enhancer compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones m+n is preferably from 11 to 15 and p is preferably 0.

Enhancers of the above structural formula are referred to herein as "Hsieh enhancers" and are described, for example, in aforementioned U.S. Pat. Nos. 5,023,252 and 5,731,303 (hereinafter the "Hsieh Patents"). Such enhancers are lipophilic and are "membrane-compatible," meaning that they do not cause damage to the membrane on which the composition of the present invention is to be applied (hereinafter the "target membrane"). Such enhancers also produce a low level of irritability or no irritability to the target membrane, and in fact serve as emollients.

Preferred enhancers for use in the present invention are macrocyclic enhancers. The term "macrocyclic" is used herein to refer to cyclic compounds having at least 12 carbons in the ring. Examples of preferred macrocyclic enhancers for use in the present invention include: (A) macrocyclic ketones, for example, 3-methylcyclopentadecanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cyclopentadecanolide, ω-pentadecalactone).

Oxacyclohexadecan-2-one and cyclopentadecanone are especially preferred.

Although the above are preferred permeation enhancers, one of ordinary skill in the art would recognize that the instant teachings would also be applicable to other permeation enhancers. Non-limiting examples of other permeation enhancers useful in the instant invention are the simple long chain esters that are Generally Recognized As Safe (GRAS) in the various pharmacopoeial compendia. These may include simple aliphatic, unsaturated or saturated (but preferably fully saturated) esters, which contain up to medium length chains. Non-limiting examples of such esters include isopropyl myristate, isopropyl palmitate, myristyl myristate, octyl palmitate, and the like. The enhancers are of a type that are suitable for use in a pharmaceutical composition. The artisan of ordinary skill will also appreciate that those materials that are incompatible with or irritating to mucous membranes should be avoided.

The enhancer is present in the composition in a concentration effective to enhance penetration of the pharmaceutically active agent that is to be delivered through the nasal mucosa. Various considerations should be taken into account in determining the amount of enhancer to use. Such considerations include, for example, the amount of flux (rate of passage through the membrane) achieved and the stability and compatibility of the components in the formulations. The enhancer is generally used in an amount of about 0.001 to about 40 (w/w) % of the composition. Specific ranges include, about 0.01% to about 30 (w/w), about 0.1 to about 25% (w/w), about 1% to about 15% (w/w), about 5 to 10% (w/w). Alternatively, the amount of the enhancer may range from about 1.0 to about 3% (w/w) or about 10 to about 20% (w/w).

In forming an emulsion in which the water-insoluble enhancer is a normally solid material, the enhancer is dissolved in a suitable solvent. If the enhancer is a normally liquid material which is water-immiscible, a suitable solvent for the enhancer may or may not be used, as appropriate. In certain embodiments, the enhancer is dissolved, dispersed, suspended, or solubilized in suitable solvent(s) such as alcohols, oils, glycerol, ethylene glycol, propylene glycol, hexane, acetone, freon, water, other polar or non-polar solvents, or a mixture, which is then added to a composition comprising an effective amount of the desired antigen admixed with a pharmaceutical carrier. In some cases, when the enhancers are in the liquid form, a "neat" solution of enhancer can be directly incorporated in the antigen, pharmaceutical carrier, and enhancer mixture, in which the concentration of enhancer ranges from about 0.1% to about 50% (w/w).

Pharmaceutical carriers include suitable non-toxic vehicles in which an antigen is dissolved, dispersed, impregnated, or suspended, such as water or other solvents, fatty materials, celluloses and their derivatives, proteins and their derivatives, collagens, gelatine, polymers, adhesives, sponges, fabrics, and the like and excipients which are added to provide better solubility or dispersion of the drug in the vehicle. Such excipients may include non-toxic surfactants, solubilizers, emulsifiers, chelating agents, binding materials, lubricants softening agents, and the like.

A liquid carrier may be present in the composition in a concentration effective to serve as a suitable vehicle for the compositions of the present invention. In general, the carrier is used in an amount of about 40 to about 98 wt. %, or about 50 to about 98 wt. % of the composition. The compositions of the present invention are preferably delivered as nasal sprays.

The liquid carrier may be water or any other suitable liquid, solvent, or mixture thereof. An antigen may be dispersed or dissolved in the liquid carrier in a therapeutically effective amount. The water may contain suitable buffering agents to result in a pH wherein the particular antigen is delivered optimally, or it may contain other carriers, such as glycerin, propylene glycol, polyethylene glycols of various sizes, amino acid modifiers, such as arginine and the like, and other suitable soluble excipients, as is known to those who are proficient in the art of compounding or pharmaceutics.

Non-limiting examples of peptides useful in the present invention include: Anti-Inflammatory Peptides such Anti-Inflammatory Peptide 1; Anti-Aging Peptides; Apelin Peptides such as Apelin-12; Atrial Natriurectic Peptides such as Urodilatin; Bombesin and Analogs thereof; Brain Injury Derived Peptide; Calcitonin; Defensins; Deltorphins, Dermorphins and Analogs thereof including other opiod peptides such as Acetalins, BAM Peptides, .alpha.-Casein Exorphins, .beta.-Casomorphins, Dynorphins, Endomorphins, Endorphins, Enkephalins, Gluten Exorphins, Kyotorphins, Methorphamide, Neoendorphins, Syndyphalins, H-Tyr-D/L-Tic-OH, and Valorphin; Dynorphin and Analogs and Sequences thereof; Enterostatins; GHrelins; Glucagons and Glucagon-Like Peptides such as GLP-1 and GLP-2; Gonadotropin Releasing Hormones; Growth Hormones; Growth Hormone Releasing Hormones; Insulino-Tropic Compounds; Kyotorphins; Leptin and Fragments thereof; Lutein; Myelin Basic Protein Fragments; Physalaemin and Fragments thereof; Secretins; Thymosins and Fragments thereof such as Thymosin.beta.4; Transforming Growth Factors (TGF) and Fragments thereof; Tuftsin; Tumor Necrosis Factors (TNF) and Related Peptides; and VIP, Prepro VIP, and Analogs and Fragments thereof.

The composition of the present invention may exist in various forms, for example, an oil-in-water emulsion, a water-in-oil emulsion, and a water-in-oil-in-water emulsion. The active compounds of the compositions of the present invention may exist in either the continuous or the dispersed phase or in both phases depending upon whether the compounds are hydrophilic, lipophilic, or amphiphilic. In an example of a preferred embodiment of the present invention, the emulsion comprises oil droplets dispersed in a continuous aqueous phase with a lipophilic enhancer being contained in the oil droplets and a water-soluble pharmaceutically-active compound dissolved in the continuous aqueous phase. In a preferred embodiment wherein an oil phase is utilized, the concentration of the oil in the oil phase is such that it does not promote crystallization.

The composition of the present invention may also comprise an emulsifying agent for use in aiding the formation of an emulsion. Essentially any suitable hydrocolloid emulsifying agent, typically a solid material, or a mixture of two or more such emulsifying agents can be used in the practice of the present invention. Hydrocolloid emulsifying agents include: vegetable derivatives, for example, acacia, tragacanth, agar, pectin, and carrageenan; animal derivatives, for example, gelatin, lanolin, cholesterol, and lecithin; semi-synthetic agents, for example, methylcellulose and carboxymethylcellulose; and synthetic agents, for example, acrylic emulsifying agents such as carbomers. The hydrocolloid emulsifying agent forms hydrocolloids (hydrated lyophilic colloids) around the emulsified liquid droplets of the emulsion. The hydrocolloid serves as a protective layer around each emulsified droplet which physically repulses other droplets, thus hindering Ostwald ripening (the tendency of emulsified droplets to aggregate). In contrast, other emulsifying agents typically protect the emulsified droplets by forming a liquid crystalline layer around the emulsified droplets. In compositions which employ a liquid crystalline layer-forming emulsifying agent, the hydrophilic-lipophilic balance (HLB) of the oil phase of the emulsion must be matched with that of the emulsifying agent to form a stable emulsion and, often, one or more additional emulsifying agents (secondary emulsifying agents) must be added to further stabilize the emulsion. The aforementioned liquid crystalline layer also retards the release of the compounds of the dispersed phase upon contact with the target substrate.

The hydrocolloid emulsifying agents for use in the composition of the present invention include compounds which exhibit a low level of irritability or no irritability to the target membrane and which have good bioadhesive and mucoadhesive properties. Examples of hydrocolloid emulsifying agents which exhibit such properties include cellulosic emulsifying agents and acrylic emulsifying agents, including, for example, those which have an alkyl group containing from about 10 to about 50 carbon atoms. Particularly preferred acrylic emulsifying agents for use in the present invention are copolymers of a carboxylic acid and an acrylic ester (described, for example, in U.S. Pat. No. 3,915,921 to Schlatzer and U.S. Pat. No. 4,509,949 to Huang et al.), with those which are cross-linked being especially preferred. An example of such an especially preferred emulsifying agent for use in forming an oil-in-water emulsion is "acrylates/$C_{10\text{-}30}$ alkyl acrylate crosspolymer", a cross-linked polymer of acrylic acid and ($C_{10\text{-}30}$) alkyl acrylates. Acrylates/$C_{10\text{-}30}$ alkyl acrylate crosspolymer is available from Noveon, Inc. (previously B.F. Goodrich) and is sold under the trade name Pemulen®. Acrylates/$C_{10-30}$ alkyl acrylate crosspolymer has a small lipophilic portion and a large hydrophilic portion, thus allowing for it to function as a primary emulsifier for the formation of oil-in-water emulsions. In addition, acrylates/$C_{10-30}$ alkyl acrylate crosspolymer is capable of releasing the compounds of the dispersed phase upon contact with a substrate, namely, biological membranes or mucosa and will not re-wet (the oil phase will not re-emulsify upon contact with water). Additional information regarding acrylates/$C_{10-30}$ alkyl acrylate crosspolymer, which is listed in the U.S. Pharmacopeia, is provided in Noveon publications TDS-114, 117, 118, 124, 232-3, and 237, and PDS Pemulen 1622.

In forming an emulsion in which the water-insoluble enhancer is a normally solid material, the enhancer is dissolved in a suitable solvent. If the enhancer is a normally liquid material which is water-immiscible, a suitable solvent for the enhancer may or may not be used, as appropriate.

The emulsifying agent is present in the composition in a concentration that is effective to form the desired liquid emulsion. In general the emulsifying agent is used in an amount of about 0.001 to about 5 wt. % of the composition, and more generally in an amount of about 0.01 to about 5 wt. % of the composition, and most generally in an amount of about 0.1 to about 2 wt. % of the composition.

The composition of the present invention may include, as an optional ingredient, particulate solids dispersed in the composition. For example, the composition may include an additional pharmaceutically-active compound dispersed in the liquid continuous phase of the emulsion in the form of microcrystalline solids or nanoparticulates.

While the hydrocolloid emulsifying agent forms a protective layer around the emulsified liquid droplets, thus forming a stable emulsion by hindering Ostwald-ripening without the need for further stabilizing agents, in some instances it may be desirable to further improve the stability of the emulsion. Such may be accomplished by the addition of Ostwald-ripening inhibitors and/or surfactants.

An Ostwald-ripening inhibitor is a material which reduces the tendency of emulsified droplets to aggregate and form larger droplets. Essentially any suitable Ostwald-ripening inhibitor or a mixture of such inhibitors may be used to improve further the physical stability of the emulsion. Preferred Ostwald-ripening inhibitors are hydrophobic agents such as hydrocarbons and hydrocarbon waxes. Examples of hydrophobic agents are petrolatum, hexadecane, and long-chain esters, for example, octyl palmitate. The Ostwald-ripening inhibitor is present in the composition in a concentration effective to prevent the emulsified droplets, particularly relatively small droplets (for example, one micron in diameter), from aggregating into larger droplets which may result in settling (materials settling to the bottom) or creaming (oils rising to the top). For guideline purposes, it is believed most applications will involve the use of the Ostwald-ripening inhibitor in an amount of about 0.001 to about 5 wt. % of the composition and more likely in an amount of about 0.1 to about 1 wt. % of the composition.

In one preferred embodiment, the permeation enhancer is emulsified in the aqueous phase that contains the antigen. The emulsification may be effected through the use of one or more suitable surfactants. The selection of a suitable surfactant is deemed to be within the scope of those skilled in the art based on the teachings herein. Such surfactants include for example, anionic, cationic, and non-ionic surfactants. Preferred surfactants are non-ionic surfactants. Alone or in combination with one or more other surfactants, those having a hydrophilic-lipophilic balance number (HLB) of from about 4 to about 18 are preferred, those between 7 and 14 more preferred, and those between 9 and 13 most preferred. Examples of such non-ionic surfactants are PEG-60 corn glycerides, PEG-20 sorbitan monostearate, phenoxy-poly(ethyleneoxy)ethanol, sorbitan monooleate, and the like. Especially preferred are compendial surfactants such as those described in compendia such as the Food Chemicals Codex, National Formulary, U.S. Pharmacopeia, and the Code of Federal Regulations. It is preferred that the average diameter of the droplets of the emulsion be from about 50 nanometers (nm) to about 20 micrometers (μm) and more preferably from about 200 nm to about 5 μm. In general each surfactant is present in an amount no greater than about 2 wt. % of the composition and more generally no greater than about 1 wt. % of the composition. Also, it is important to prefer the nature of the side-chains of the surfactants to those with no double bonds, and this invention is most preferred to include those without unsaturated carbon-carbon bonds. The reason for this is that unsaturated fatty acid side chains (called also "olefinic" fatty acids) tend to oxidize over time, rendering them unsuitable. They tend to become colored, or dark, and give rise to intermediates that may react with the important antigen in the same formulation, rendering it less useful or unsuitable from a regulatory vantage point (in the US, for example, the key regulatory body being the FDA, and in other countries its counterpart). Olefins are suspected to have the additional liability of contributing to irritation which must be avoided for intranasal applications. However, unsaturated side-chain surfactants are not excluded from use in this invention. For example, polysorbate 80, containing a monounsaturated side chain of oleic acid ester, may be mitigated in its irritation liability by using a limited concentration of same, generally under 1% in the formulation, or by adding soothing components, such as glycerin, to the formulation to negate such undesired effect.

In one preferred embodiment, the emulsified or discontinuous phase that contains the permeation enhancer is in the form of droplets. In general, smaller droplets confer greater stability. Larger droplets may cause instability and may decrease shelf-life. In preferred embodiments the lipid droplet size ranges from 0.025 microns (25 nm) to 20 microns and preferably from 0.1 microns to 5 microns.

In some instances the permeation enhancers, the antigens and/or other components of the compositions used in the instant invention may crystallize at room temperature or at higher temperatures. In order to inhibit or prevent such crystallization, the composition may include one or more crystallization inhibitors. Crystallization, if allowed to proceed, renders the emulsion unstable and has an adverse effect on shelf life. Preferred crystallization inhibitors function by lowering the temperature at which the involved agent crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. Another example of such a crystallization inhibitor is polyethylene glycol 1000. The selection of a suitable crystallization inhibitor is deemed to be within the scope of those skilled in the art from the teachings herein.

For example, crystallization inhibitors may be capable of lowering the temperature of crystallization of the involved agent to below about 25° C., or to below about 5° C. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate, each of which may be used in pharmaceutical preparations.

The crystallization inhibitor is present in the composition in a concentration effective to inhibit the crystallization of at least one component of the composition. In general the crystallization inhibitor is present in an amount of about 0.001 to about 5 wt. %, or from about 0.01 to about 2 wt % of the composition. In one embodiment, the crystallization inhibitor is present in an amount of from about 0.1 to about 1 wt. % of the composition. For example, a crystallization inhibitor is preferably used when the enhancer has a crystallization temperature above about 0 degrees Centigrade. In particular, for example, a crystallization inhibitor is preferably used when the enhancer is, pentadecalactone and/or cyclohexadecanone, since these crystallize above room temperature.

The compositions of the present invention may contain an enzyme inhibitor. As is well known to practitioners in peptide and protein biochemistry, peptides tend to be very sensitive to the presence of enzymes, such as proteolytic enzymes, that rapidly degrade the peptide when present in even minute amounts. Typical enzyme inhibitors that are commonly employed and that may be incorporated into the present invention include, but are not limited to leupeptin, aprotinin, and the like. Enzyme inhibitors also include nuclease inhibitors.

The intranasal delivery method is not particularly limited as long as it can induce an immune response, for example, an immune response in the topical mucous membrane of the respiratory tract (particularly upper respiratory tract), which is an infection route of many immunogen such as bacterium and virus. Examples of the method include spraying, swabbing, dropwise addition and the like. The pharmaceutical composition can be administered intranasally by devices including, but not limited to, an intranasal spray device, an atomizer, a nebulizer, a metered dose inhaler (MDI), a pressurized dose inhaler, an insufflator, an intranasal inhaler, a nasal spray bottle, an unit dose container, a pump, a dropper, a squeeze bottle, or a bi-directional device. The pharmaceutical composition may be administered intranasally in the form of a gel, an ointment, a nasal emulsion, a lotion, a cream, a nasal tampon, or a bioadhesive strip. The nasal delivery device can be metered to administer an accurate effective dosage amount to the nasal cavity. The nasal delivery device can be for single unit delivery or multiple unit delivery. The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

In one embodiment, the composition of the present invention is delivered through a nasal spray applicator. If intranasal application is desired, the composition may be placed in an intra-nasal spray-dosing device or atomizer and may be applied by spraying it into the nostrils of a subject for delivery to the mucous membrane of the nostrils. A sufficient amount is applied to achieve the desired systemic or localized antigen levels. For an intra-nasal spray, up to about 200 microliters is typically applied, with an application of about 50 to about 150 microliters being preferred, and 75 to 120 microliters most preferred. One or more nostrils may be dosed and application may occur as often as desired or as often as is necessary. In preferred embodiments, the nasal spray applicator is selected to provide droplets of the composition of a mean size of from about 10 microns to about 200 microns. More generally the droplet size is from about 30 microns to about 100 microns.

The present invention provides a pharmaceutical composition for nasal immunization which is capable of inducing an effective immune response. In certain circumstances, an effective immune response may be protective. An immune response may be measured in vitro, in vivo and/or ex vivo. Examples of measurable immune responses include, but are not limited to, antigen-specific antibody production (including measuring specific antibody subclasses), secretion of cytokines (including, but not limited to, IL-1, IL-2, IL-4, IL-5, IL-6, IL-10, IL-12, IFN-$\alpha$, IFN-$\beta$, IFN-$\gamma$, TNF-$\alpha$), release of histamine, activation or expansion of lymphocyte populations such as NK cells, T lymphocytes, B lymphocytes, macrophages and the like. Methods for measuring specific antibody responses include enzyme-linked immunosorbent assay (ELISA) and are well known in the art. Measurement of numbers of specific types of lymphocytes such as $CD^{4+}$ T cells can be achieved, for example, with fluorescence-activated cell sorting (FACS). Cytotoxicity assays can be performed for instance as described in Raz et al. (1994) *Proc. Natl. Acad. Sci. USA* 91:9519-9523. Serum concentrations of cytokines can be measured, for example, by ELISA. These and other assays to evaluate the immune response to an immunogen are well known in the art. See, for example, *Selected Methods in Cellular Immunology* (1980) Mishell and Shiugi, eds., W.H. Freeman and Co. U.S. Pat. No. 7,628,990.

A therapeutically effective amount of the antigen or antibody may vary according to factors such as the kind of antigen, desired action, physical and medical conditions of the subject, such as age, body weight, etc. A therapeutically effective amount of an antigen or antibody can be determined by one of ordinary skill in the art without undue experimentation. Based on known immunization dosing regimen and the teachings herein, one skilled in the art can select the dosing regimen and dosage for a particular subject or subjects. The ability of antigen to induce an effective immune response or of an antibody to inhibit a measurable parameter can be evaluated in an animal model system predictive of efficacy in humans. For example, the ability of an anthrax antigen to protect rabbits from challenge with *B. anthracis* can predict efficacy in humans as described in the Examples. Alternatively, this property of an antigen or antibody can be evaluated by examining the ability of the composition to modulate antigen/cell interactions, e.g., binding, infection, virulence, and the like, by in vitro assays known to the skilled practitioner. In vitro assays include binding assays, such as ELISA, and neutralization assays.

The subjects for administration of the composition of the present invention include mammals such as human, monkey, mouse, rat, rabbit, cat, bovine, dog, horse, goat and the like, and birds such as chicken and the like.

In some embodiments, a composition of the present invention is administered to a subject via more than one route. For example, a subject that would benefit from having a protective immune response (e.g., immunity) towards a pathogenic microorganism may benefit from receiving mucosal administration (e.g., nasal administration) and, additionally, receiving one or more other routes of administration (e.g., parenteral or pulmonary administration). In some embodiments, administration via nasal route is sufficient to induce both mucosal as well as systemic immunity towards an antigen. In other embodiments, administration via multiple routes serves to provide both mucosal and systemic immunity.

Although a preferred embodiment is a preformulated composition, it is also within the scope of the present invention that a subject may be treated with the hereinabove-described and hereinbelow-described combination that is not preformulated; i.e., an antigen in liquid carrier and the enhancer may be mixed at the time of application, such as where the mixing occurs in an atomizer at the time the composition is sprayed.

EXAMPLES

The Examples below are illustrative of compositions of the present invention. The concentrations of the ingredients comprising the compositions are given in percent by weight relative to the total weight of the composition.

Example Nos. 1 and 2 are examples of compositions of the present invention for use in an intra-nasal spray.

In Example Nos. 1 and 2, the ingredients of Part A were mixed by mechanically stirring at 40° C. until homogeneous. The ingredients of Part B were mixed separately using magnetic stirring at 40° C. until homogeneous and then added to Part A. The resulting mixture was stirred vigorously and Part C was added slowly to the mixture. Following the addition of Part C, Part D was added and the resulting mixture was stirred for 4 hours at 40° C. The mixture was allowed to cool to room temperature while stirring for an additional 18 hours. Part E was then added while shaking and stirring for 4 hours. The resulting mixture is referred to as the "Premix".

A solution of pharmaceutically-active compound in the concentration desired was prepared separately. The pharmaceutically-active compound was mixed with and dissolved in water by agitating until homogeneous. A pH modifier was then added and the resulting mixture was mixed by rolling on a roller mill at 120 rpm at room temperature until the solution was homogeneous.

The Premix was added to the aqueous solution of pharmaceutically-active compound at room temperature and the resulting mixture was mixed by rolling on a roller mill at 120 rpm until the final mixture composition was homogeneous.

Example 1

This example describes the preparation of a composition which can be used as an intra-nasal spray for the delivery of GHRP-6 (H-His-D-Trp-Ala-Trp-D-Phe-Lys-NH$_2$).

Premix

|  | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| Part B | |
| propylene glycol, USP - solvent | 1.00% |
| glycerin, USP - cosolvent, emollient, humectant and protein stabilizer | 2.00% |
| water, sterile and deionized | 44.05% |
| Part C | |
| acrylates/C$_{10-30}$ alkyl acrylate crosspolymer - Permulen TR2, NF grade (Noveon, Inc.) - emulsifier and thickener | 0.10% |
| Part D | |
| benzalkonium chloride, 50% aqueous solution - Maquat (Mason) - preservative | 0.01% |
| Part E | |
| triethanolamine, NF - pH modifier | 0.03% |

Solution of Pharmaceutically-Active Compound

| water, sterile and deionized | 49.10% |
|---|---|
| GHRP-6 (Bachem) - pharmaceutically-active compound | 0.87% |
| triethanolamine, NF - pH modifier | 0.03% |

The resulting composition comprised a stable emulsion in which the dispersed phase consisted of liquid droplets which were uniformly dispersed in the composition and which consisted of the enhancer dissolved in the solvents comprising the crystallization inhibitor and the Ostwald-ripening inhibitor. The continuous phase comprised an aqueous solution of propylene glycol, glycerin, preservative, and pharmaceutically-active compound. The pH modifier was considered to be associated with the emulsifier. One hundred microliters of the composition contained approximately 100 micrograms of GHRP-6.

Example 2

This example describes the preparation of a composition which can be used as an intra-nasal spray for the delivery of oxycodone. Oxycodone was used in the form of its free base prepared from the commercially available hydrochloride salt by dissolving in 20 parts of water and a stoichiometric amount of 1.0 N sodium hydroxide. The precipitate was collected and washed with water. The precipitate was then dried at room temperature using a vacuum pump.

Oxycodone Intra-Nasal Preparation

|  | Wt % |
|---|---|
| Part A | |
| oxacyclohexadecan-2-one (Firmenich) - enhancer | 2.00% |
| cottonseed oil, super refined (Croda) - solvent, crystallization inhibitor | 0.67% |
| petrolatum - Protopet (Witco) - solvent, Ostwald-ripening inhibitor | 0.14% |
| oxycodone, free base - pharmaceutically-active compound | 2.00% |
| Part B | |
| acrylates/C$_{10-30}$ alkyl acrylate crosspolymer - Permulen TR2, NF Grade (Noveon, Inc.) - emulsifier and thickener | 0.08% |
| Part C | |
| glycerin, USP - cosolvent, emollient, humectant and protein stabilizer | 2.10% |
| water, sterile and deionized | 93.00% |
| benzalkonium chloride, 50% aqueous solution - Maquat (Mason) - preservative | 0.01% |

The ingredients of Part A were combined at 40° C. by mechanical stirring until a paste was formed. Part B was then combined with Part A by mechanically stirring at 40° C. until a homogeneous paste was formed. Part C was then added and the resulting mixture was stirred mechanically at room temperature until a white homogeneous emulsion was formed.

The free base of oxycodone, which is insoluble in water, is strong enough to stabilize emulsions formed using acrylates/C$_{10-30}$ alkyl acrylate emulsifier. This enables the composition to exist in the form of a cohesive homogeneous emulsion without the need for use of further pH modifiers and in order to avoid the formation of an inorganic salt. The dispersed phase consisted of the enhancer dissolved in the solvents comprising the crystallization inhibitor and the Ostwald-ripening inhibitor. The continuous phase consisted of glycerin, preservative, and water. The pharmaceutically-active compound was considered to be associated with the acrylates/C$_{10-30}$ alkyl acrylate crosspolymer emulsifier.

One hundred microliters of the composition contained approximately 2 milligrams of oxycodone.

Example 3

Nasal Immunization with Recombinant Anthrax Antigen

Materials and Methods

Anthrax protective antigen from *Bacillus anthracis*, rPa, will be purchased from Calbiochem (www.emdchemicals.com). As described above, a Premix containing oxacyclohexadecan-2-one will be prepared. A solution containing rPA will be prepared separately. rPA will be (i) formulated in PBS without adjuvant, (ii) adsorbed onto aluminum hydroxide (70 mg of aluminum hydroxide/10 mg of rPA) (Alhydrogel; Superfos Biosector) as adjuvant, or (iii) formulated with unmethylated, phosphorothioate-linked, CpG-containing oligonucleotides (hereafter, "CpG"; 10 mg of CpG/10 mg of rPA) (number 1826, SEQ ID NO. 1 5'-TCCATGACGTTC-CTGACGTT-3'; Proligo) as adjuvant. The Premix will be added to the solution containing rPA at room temperature and the resulting mixture will be mixed by rolling on a roller mill at 120 rpm until the final mixture composition was homogeneous. The specific amounts of each ingredient in the formulation can be determined without undue experimentation by one of ordinary skill in the art.

Animals and Immunizations

Female BALB/c mice (Charles River Laboratories), 6-8 weeks old (10 mice/group), will be immunized with 10 µg of rPA on days 0, 21, and 42. For intranasal delivery, liquid will be instilled (15 µL in each nostril) into the nasal cavities of anesthetized mice. Anesthetized mice will be bled via their retroorbital sinuses on days 21, 42, and 56.

Female New Zealand White rabbits (Myrtles Rabbitry) (6-9 rabbits/group) will be immunized with 50 µg of rPA on days 0, 21, and 42. rPA will be formulated in PBS without adjuvant, with Alhydrogel (350 mg of aluminum hydroxide/ 50 mg of rPA) or CpG (50 mg of CpG/50 mg of rPA). A Penn-Century nasal sprayer will be used for intranasal delivery of liquid vaccine (100 µL into a single nostril). Rabbits will be bled via their marginal ear veins on days 21, 42 and 56.

ELISA

ELISA analysis of rPA-specific antibody titers will be conducted. Maxisorp 96-well plates (Nunc) will be coated with 1 mg/mL rPA in 0.05 mol/L carbonate coating buffer (pH 9.6) at 4° C. overnight. Plates will be blocked for 1.5 h at 37° C. in blocking buffer (5% skim-milk powder in PBS-Tween 20) and then will be washed 3 times with PBS-Tween 20. Samples will be serially diluted 2-fold in duplicate across the plate in blocking buffer and will be incubated for 1 h at 37° C. After 3 washings, plates will be incubated with horseradish peroxidase (HRP)-conjugated goat anti-mouse or anti-rabbit IgG (Southern Biotechnology) for 45 min at 37° C. After washing, plates will be developed for 30 min at room temperature with 3,3',5,5'-tetramethylbenzidine substrate (Sigma) and will be stopped by the addition of 0.5 mol/L $H_2SO_4$; optical densities will be read at 450 nm. End-point titers will be defined as the highest dilution of a sample yielding an OD450 nm value at least 3 times the background obtained for serum samples from unimmunized control animals. Antibody isotypes will be determined by use of HRP-labeled goat anti-mouse $IgG_1$ or $IgG_{2a}$ antibodies and mouse reference standards (Bethyl Laboratories).

Toxin-Neutralizing Antibody (TNA) Assay

TNA titers will be determined by use of a modified version of a method described in Little et al., Production and characterization of monoclonal antibodies against the lethal factor component of *Bacillus anthracis* lethal toxin. *Infect. Immun.* 1990; 58:1606-13. Confluent J774A.1 cells will be plated ($7\times10^4$ cells/well) in sterile, 96-well, clear-bottom, black plates (Corning Costar) at 37° C. and in 5% $CO_2$. A fresh solution containing 100 ng/mL LF (List Biological Laboratories) and 200 ng/mL rPA will be mixed with an equal volume of diluted samples in triplicate and will be incubated for 1 h at 37° C. Medium will be then replaced with 100 mL of diluted solution of LF, PA, and test sample, which will be incubated for 4 h at 37° C. in 5% CO2. Cell viability will be determined by ATP content (ViaLight HS; Cambrex Bio Sciences Rockland), with untreated cells used as a reference control. End-point TNA titers will be defined as the reciprocal of the highest serum dilutions producing a significant neutralization (by t test) of PA-LT binary toxin cytotoxicity that is 3-fold greater than that of control serum samples.

*B. anthracis* Aerosol Challenge

To determine the protective efficacy of nasal immunization, a lethal challenge study will be performed in rabbits. Aerosol challenge will be performed as described in Pitt et al., In vitro correlate of immunity in a rabbit model of inhalational anthrax. *Vaccine* 2001; 19:4768-73. The determination of the presented aerosol dose will be calculated by use of respiratory minute volume (Vm) estimates that will be derived from the respiratory function measurements performed before the exposures. The presented aerosol dose will be then calculated by multiplying the total volume (Vt) of experimental atmosphere inhaled by each animal (Vt/Vm X length of exposure) and the empirically determined exposure concentration from chamber sampling (Ce) (presented dose=CexVt). Dose is expressed as a multiple of lethal doses, on the basis of $1.1\times10^5$ cfu equaling 1 lethal dose. Rabbits will receive a mean±SD inhaled dose of 103±45 $LD_{50}$. Survival rates will be compared by use of Fisher's exact test, with bootstrap adjustments for multiple comparisons. Time to death comparisons will be made by use of at t test, with bootstrap adjustments for multiple comparisons.

Example 4

Immunization with *E. coli* Antigen

Enterotoxigenic *Escherichia coli* (ETEC) is a major cause of travellers' diarrhoea. ETEC are transmitted via contaminated food and beverages. They colonize the small intestine and secrete heat-labile enterotoxin (LT) or heat-stable enterotoxin (ST)—or a combination—which cause secretory diarrhoea.

A nasal vaccine containing heat-labile enterotoxin (LT) from ETEC delivered intranasally will be studied.

Antigen

Native LT of *E. coli* will be produced from *E. coli* strain HE22 TP 235 Km. LT will be mixed with oxacyclohexadecan-2-one and other components for the preparation of a nasal formulation as described above.

Participants

Healthy adults (aged 18-45 years) will be enrolled for this study. Exclusion criteria will include history of travellers' diarrhoea, travel to an endemic country in the previous 12 months; previous use of a cholera, LT, or ETEC vaccine; significant illness; immunosuppression, etc.

Vaccine Administration.

The vaccine will be administered in two doses. The first dose will be administered on day 0, and the second immunization on day 15.

Postvaccination Follow-Up.

Volunteers will be observed for 20 min after each dose for occurrence of immediate adverse effects. The volunteers will be given a diary to record signs and symptoms observed after vaccination. Reported symptoms will be graded as mild (noticeable), moderate (affecting normal daily activities), or severe (suspending normal daily activities). The volunteers will be evaluated at 24 and 48 h for clinical assessment and evaluation of possible side effects. Volunteers who show signs of vaccine skin reactions will be instructed to return to the clinic at 72 h for additional clinical assessment. Volunteers will be then followed as needed until side effects had completely resolved.

ASC Immune Responses.

The responses of antibody-secreting cells (ASCs) to the vaccine antigens will be chosen as an immunological endpoint for this study, since previous studies have shown that ASC responses correlate with mucosal intestinal immune responses. Wenneras, et al. 1992. Antibody-secreting cells in human peripheral blood after oral immunization with an inactivated enterotoxigenic *Escherichia coli* vaccine. *Infect. Immun.* 60:2605-2611. Venous blood samples will be obtained from the volunteers on day 0 before immunization and on days 7, 28, 35, 56, 84, 91, 98, and 112 after the first immunization. Blood specimens will be collected using EDTA-treated tubes (Becton Dickinson Vacutainer Systems, Rutherford, N.J.). Peripheral blood mononuclear cells (PBMC) will be isolated from the blood sample by gradient centrifugation on Ficoll-Hypaque (Sigma Chemical Co., St. Louis, Mo.) and will be assayed for total and vaccine-specific numbers of IgA and IgG ASCs by the enzyme-linked immunospot (ELISpot) technique. Individual wells of nitrocellulose-bottomed 96-well plates (Millititer HA; Millipore Corp., Bedford, Mass.) will be coated with 0.1 ml of purified CS6 (20 µg/ml) or GM1 ganglioside (0.5 µg/ml) and will be incubated overnight at 4° C. After a PBS wash, GM1-coated wells will be exposed to LT (0.5 µg/ml) for 2 h at 37° C. After being washed with PBS, the plates will be blocked with complete RPMI medium (Gibco BRL, Grand Island, N.Y.) supplemented with 5% fetal calf serum (Gibco BRL) and 50 µg of gentamicin (Gibco BRL)/ml. The PBMC will be adjusted to $2 \times 10^7$ viable cells/ml in complete RPMI medium. A final 0.1 ml suspension of PBMC will be added to each well ($10^6$ PBMC added per well), and plate contents will be incubated for 4 h at 37° C. in 5.0% $CO_2$. Plates will be washed. Their contents will be incubated overnight at 4° C. with a mixture of two affinity-purified goat anti-human immunoglobulin antibodies with distinct isotype specificities, one conjugated to alkaline phosphatase (IgG) and the other conjugated to horseradish peroxidase (IgA) (Southern Biotech Associates, Birmingham, Ala.), and will be exposed to the appropriate chromogen-enzyme substrate (Sigma). Spots, corresponding to a zone of antibodies secreted by individual cells, will be enumerated in triplicate wells under X40 magnification, with data expressed as the number of spot-forming cells per $10^6$ PBMC. As previously described (Jertborn, et al. 2001. Dose-dependent circulating immunoglobulin A antibody-secreting cell and serum antibody responses in Swedish volunteers to an oral inactivated enterotoxigenic *Escherichia coli* vaccine. *Clin. Diagn. Lab. Immunol.* 8:424-428), we will define a positive ASC response as a $\geq$2-fold increase over baseline value of the ASCs per $10^6$ PBMC, when the number of ASCs is $\geq$0.5 per $10^6$ PBMC in the baseline sample. If the number of preimmune ASCs is less than 0.5 per $10^6$ PBMC, a value of >1.0 per $10^6$ PBMC after dosing will be considered a positive response.

Serum Antibody Measurements.

Venous blood samples will be obtained from the volunteers before immunization and on days 14 and 28 after each immunization for measurements of serum antibody titers. IgA and IgG antibody titers against LT will be measured by the GM1-enzyme-linked immunosorbent assay (ELISA) method (Jertborn, et al. 1998. Safety and immunogenicity of an oral inactivated enterotoxigenic *Escherichia coli* vaccine. *Vaccine* 16:255-260). LT will be used as solid-phase antigens. The LT used for the ELISAs will be from the same lots used for the vaccine preparation. Individual microtiter wells (immunoplates; Nunc, Roskilde, Denmark) will be coated with GM1 ganglioside (0.5 µg/ml) (Sigma) at room temperature overnight at 37° C. overnight. The GM1-coated wells will be then washed with PBS and incubated with 0.1 ml of LT (0.5 µg/ml) for 2 h at 37° C. After being blocked with 0.1% bovine serum albumin (Sigma), the serum samples will be threefold serially diluted (initial dilution 1:5) and will be then incubated at room temperature for 90 min. Bound antibodies will be demonstrated by addition of rabbit anti-human IgA or IgG conjugated with horseradish peroxidase (Jackson ImmunoResearch Laboratories, West Grove, Pa.) and will be incubated at room temperature for 90 min, followed by addition of o-phenylenediamine-$H_2O_2$ (Sigma). The endpoint titers will be assigned as the interpolated dilutions of the samples giving an optical density at 450 nm of 0.4 above background (absorbance at 450 nm). Titers will be adjusted in relation to a reference specimen included in each test to compensate for day-to-day variation. Pre- and postdosing serum samples from the same volunteer will be always tested side by side. The antibody titer ascribed to each sample represented the geometric mean of duplicate determinations performed on different days. Reciprocal endpoint titers that will be <5 will be assigned a value of 2.5 for computational purposes. We will define a significant response (seroconversion) as a $\geq$2-fold increase in endpoint titer between pre- and postimmunization specimens, with the added criterion that the postimmunization reciprocal titer be $\geq$10. Güereña-Burgueño et al., Safety and Immunogenicity of a Prototype Enterotoxigenic *Escherichia coli* Vaccine Administered Transcutaneously, INFECTION AND IMMUNITY, 2002, p. 1874-1880.

Example 5

Immunization with a Carbohydrate Antigen

Carbohydrate antigens such as blood group-related Tn, T, sialyl-Tn, sialyl-T antigens (family of T antigens) and glycolipidic GM2, GD2, and GD3 are associated with various cancers. Lo-Mann et al. *Cancer Research* 64:4987 (2004). Malignant transformation appears to result in a dysregulation of glycoslylation. The development of antibodies to carbohydrates may offer a new mode of attack against tumors. For example, CA-19-9 is associated with various gastrointestinal tumors, including pancreatic, stomach and colorectal. Duffy M. J., CA 19-9 as a marker for gastrointestinal cancers: a review. *Ann. Clin. Biochem.* 1998, 35 (Pt 3): 364-70. Nasal formulations containing CA-19-9 will be prepared as follows.

Antigen

As described above, a Premix containing oxacyclohexadecan-2-one will be prepared. A solution containing CA-19-9 will be prepared separately. The Premix will be added to the solution containing CA-19-9 and the resulting mixture will be mixed until the final mixture composition was homogeneous.

Immunization

Female BALB/c mice (Charles River Laboratories), 6-8 weeks old (10 mice/group), will be immunized with 500 µg-2 mg of CA-19-9 formulated as described above on days 0, 21, and 42. The immunization will be carried out using an intranasal spray device.

ELISA 96-well plates (Nunc) will be coated with 0.25 mg/mL CA-19-9 in 0.05 mol/L carbonate coating buffer (pH 9.6) at 4° C. overnight. Plates will be blocked using bovine serum albumin Serum samples from immunized and control mice will be serially diluted 2-fold in duplicate across the plate in blocking buffer and incubated for 1 h at 37° C. After washings, plates will be incubated with horseradish peroxidase (HRP)-conjugated goat anti-mouse or anti-rabbit IgG (Southern Biotechnology). After washings, plates will be developed for 30 min at room temperature with tetramethylbenzidine substrate (Sigma) and the reaction stopped; optical densities will be read at 450 nm. End-point titers will be defined as the highest dilution of a sample yielding an OD450 nm value at least 3 times the background obtained for serum samples from unimmunized control animals. Antibody isotypes were determined by use of HRP-labeled goat anti-mouse IgG1 or IgG2a antibodies and mouse reference standards (Bethyl Laboratories).

Example 6

Immunization with Polysaccharides

*Streptococcus pneumoniae* can cause pneumococcal pneumonia and pneumococcal bacteremia. Purified pneumococcal polysaccharides, which are components of the pneumococcal polysaccharide vaccine against *Streptococcus pneumoniae*, will be purchased from ATCC (www.atcc.org/culturesandproducts/microbiology/purifiedpneumococcalpolysaccharides/tabid/185/default.aspx). PNEUMOVAX® 23 (Pneumococcal Vaccine Polyvalent) may also be purchased from Merck. PNEUMOVAX® 23 consists of a mixture of highly purified capsular polysaccharides from the 23 most prevalent or invasive pneumococcal types of *Streptococcus pneumoniae*. Nasal formulations containing pneumococcal polysaccharides will be prepared as follows.

Antigen

As described above, a Premix containing oxacyclohexadecan-2-one will be prepared. A solution containing pneumococcal polysaccharides will be prepared separately. The Premix will be added to the solution containing pneumococcal polysaccharides and the resulting mixture will be mixed until the final mixture composition was homogeneous.

Immunization

Mice or human subjects will be nasally immunized with the formulation containing pneumococcal polysaccharides and antibody titers tested. The Advisory Committee on Immunization Practices (ACIP) has vaccine specific recommendations for the prevention of pneumococcal disease. Available from: www.cdc.gov/mmwr/PDF/rr/rr4608.pdf and www.cdc.gov/vaccines/recs/provisional/downloads/pneumo-Oct-2008-508.pdf.

Example 7

Immunization with DNA Vaccine

DNA vaccines offer a novel way to generate an protective immune response. In Example 3, supra., mice were immunized with recombinant rPA from *Bacillus anthracis*. In the following experiments, mice will be nasally immunized with a DNA plasmid encoding a detoxified form of protective antigen (PA) and antibody titers tested.

A recombinant plasmid encoding for the protective antigen will be prepared and nasal formulations developed as described above. Hermanson et al. *PNAS* 101 (37):13601-13606 (2004). Mice will be nasally immunized with the formulation containing the recombinant protective antigen and the antibody titers tested as previously described.

Example 8

Immunization with DNA Vaccine with Bacteriophage Lambda as Delivery Vehicle

In DNA vaccination, a plasmid containing a vaccine gene under the control of a eukaryotic expression cassette may be used to vaccinate the host ("naked DNA" vaccination). Whole bacteriophage•particles may also be used as DNA vaccine delivery vehicles. In this system, the gene encoding the vaccine antigen, in a suitable eukaryotic expression cassette, is cloned into a standard•gt11 bacteriophage and the whole bacteriophage particle is used to inoculate the host. The DNA is contained within a stable protein matrix which both protects it from nuclease degradation and also targets the vaccine to antigen presenting cells (APCs).

Vaccine inserts, such as Hepatitis B Surface antigen (•-HbsAg), will be cloned into the EcoRI site of a •gt11 bacteriophage, which will then be grown on a large scale and purified. Nasal formulations will be developed as described above, and be used to immunize rabbits or mice intranasally. The antibody titers will be tested as previously described.

Due to their large cloning capacity, phage vectors offer the potential for multiple vaccines within a single construct, the use of large intron-containing eukaryotic genes, and the co-administration of molecular adjuvants (e.g. IL-12/IL-15), all within a single bacteriophage particle. Hybrid phage vaccines will also be tested. The large cloning capacity of phage A, combined with it's ability to display many copies of relatively high molecular weight proteins, makes it possible to deliver a DNA vaccine combined with a protein vaccine or protein adjuvant on the same phage particle. www.mri.sari.ac.uk/pdf/bact-jclark-poster1.pdf. Clark et al. Bacterial viruses as human vaccines? *Expert Rev. Vaccines.* 2004 August; 3(4): 463-76. March et al. Genetic immunisation against hepatitis B using whole bacteriophage lambda particles. *Vaccine.* 2004 Apr. 16; 22(13-14):1666-71. Clark et al. Bacteriophage-mediated nucleic acid immunisation. *FEMS Immunol. Med. Microbiol.* 2004 Jan. 15; 40(1):21-6. Jepson et al. Bacteriophage lambda is a highly stable DNA vaccine delivery vehicle. *Vaccine.* 2004 Jun. 23; 22(19):2413-9.

Example 9

Immunization with Inactivated Virus

This example uses inactivated whole H1N1 influenza virus as the antigen for nasal immunization.

Antigen Preparation

Madin-Darby canine kidney (MDCK) cells (ATCC CCL 34) will be maintained in Dulbecco's modified essential medium (DMEM) containing 10% calf serum. Stocks of influenza virus will be prepared by inoculation with $10^5$ pfu of influenza A/PR8/34 (H1N1), in 10- or 11-day-old embryonated hen's eggs. After incubation for 40 h, the eggs will be transferred to 4° C. overnight. The allantoic fluid will be harvested and centrifuged at 1500×g for 20 min to remove cell debris. The clear supernatant will be centrifuged at 120,000×g for 1 h to pellet influenza virus particles, which will be resuspended in PBS and further purified by centrifugation using a discontinuous sucrose gradient (15%, 30% and 60%) layers. The purity of the virus will be analyzed by sodium dodecyl sulfate-polyacrylamide gel electrophoresis and Coomassie blue staining. The hemagglutination activity will be determined with chicken red blood cells (RBC) 0.5% (w/v) in phosphate buffered saline (PBS) pH 7.2 as described previously. Compans R W. Hemagglutination-inhibition: rapid assay for neuraminic acid-containing viruses. *J Virol.* 1974; 14(5):1307-9. Novak et al., Murine model for evaluation of protective immunity to influenza virus. *Vaccine* 1993; 11(1):55-60. For inactivation, the purified virus will be treated with 1:4000 (v/v) formalin and incubated for 3 days at 37° C., and then dialyzed against PBS. Inactivation of virus will be confirmed by inoculation of the virus into 10-day-old embryonated hen's eggs and plaque assay in MDCK cells. Sha et al., Induction of CD4(+) T-cell-independent immunoglobulin responses by inactivated influenza virus. *J Virol.* 2000; 74(11):4999-5005.

As described above, a Premix containing oxacyclohexadecan-2-one will be prepared. A mix containing inactivated viruses will be prepared separately. The Premix will be added to the mix containing inactivated viruses and the resulting mixture will be mixed until the final mixture composition was homogeneous.

Cholera toxin (CT) will be purchased from Sigma-Aldrich (St. Louis, Mo.). Purified mouse IgG, IgG1, IgG2a, and IgA antibodies will be obtained from Southern Biotech (Birmingham, Ala.). All ELISPOT reagents will be purchased from BD-PharMingen; the ELISA reagents for IL-6, IL-10, IL-12 and TNF-α will be purchased from eBiosciences (San Diego, Calif.) and for IFN-γ and IL-4 will be purchased from BD-PharMingen. Stable diaminobenzidine will be from Research Genetics (Carlsbad, Calif.). The receptor-destroying enzyme neuraminidase (RDE) will be purchased from Roche Diagnostics (Indianapolis, Ind.).

Immunization

Female Balb/c mice (6-8 weeks of age) will be purchased from Charles River Laboratory (Wilmington, Mass.), and used for intranasal immunizations. We will use 12 mice per group (6 mice in the same group will be used for challenge studies). For intranasal immunization, 50 μg of inactivated influenza virus with or without CT (100 μg) diluted in 50 μl of PBS will be administered three times, at weeks 0, 3 and 6.

Collection of Serum, Vaginal Lavages, Lung Lavages, Saliva and Feces

Sera will be collected 4 days before priming as pre-immune samples and 2 weeks after the first and third immunization. Blood will be collected from the retro-orbital plexus with nonheparinized microcapillaries after anesthetizing with isoflurane (Novaplus). Lung lavages will be collected by flushing the lungs with PBS. Saliva will be collected in Eppendorf tubes after intraperitoneal injection of 2 μg of carbamoylcholine chloride to stimulate secretion. Vaginal lavage samples will be collected by flushing the vagina with 200 μl of sterile PBS. Fecal samples will be collected, weighed and resuspended in 1 ml of sterile PBS with PMSF, will be vigorously vortexed to homogeneity, centrifuged at 2000×g for 10 min and the supernatants will be collected, filtered and stored at •20° C. until assayed. All samples will be mixed with the protease inhibitor phenylmethylsulfonyl fluoride (1 mM) and stored at •20° C. until assayed.

Challenge of Mice with Influenza Virus and Measurement of Lung Titers

To determine the titers of influenza virus in the lungs of infected naive and immunized mice, animals will be challenged by intranasal instillation of 25 μl of virus (600 pfu) ($1×LD_{50}$) 11 weeks after the last immunization. The challenged mice will be monitored for signs of morbidity (body weight changes, fever and hunched posture) and mortality. Mice will be weighed immediately before and daily after challenge. Half of the mice from each group will be sacrificed on day 4 and day 8 post-challenge. Lung homogenates will be prepared in DMEM serum-free medium to assess the viral titers, determined per g of lung tissue. Sha et al., Induction of CD4(+) T-cell-independent immunoglobulin responses by inactivated influenza virus. *J Virol.* 2000; 74(11):4999-5005. For plaque assays, we will prepare serial dilutions of lung supernatants, incubate them with confluent MDCK monolayer cells, and overlay with DMEM medium with 0.75% agar and 0.025% trypsin (Sigma). After 3 days of culture, the cells will be fixed with 20% ethanol, stained with 1% crystal violet in 20% ethanol and the plaques will be counted.

Evaluation of Humoral Immune Responses

The concentrations of virus-specific IgG, IgG1, IgG2a and IgA will be determined in all sera and mucosal secretions in ELISA plates coated with purified inactivated influenza virus as previously described. Sha et al., Induction of CD4(+) T-cell-independent immunoglobulin responses by inactivated influenza virus. *J Virol.* 2000; 74(11):4999-5005. Kang et al. Enhancement of mucosal immunization with virus-like particles of simian immunodeficiency virus. *J Virol.* 2003; 77(6): 3615-23. Kang et al. Intranasal immunization with inactivated influenza virus enhances immune responses to coadministered simian-human immunodeficiency virus-like particle antigens. *J Virol.* 2004; 78(18):9624-32. We will determine the hemagglutination inhibition (HI) and neutralizing antibody titers, which are both used as indicators of protective immune responses to influenza virus, as previously described. Sha et al., Induction of CD4(+) T-cell-independent immunoglobulin responses by inactivated influenza virus. *J Virol.* 2000; 74(11):4999-5005. Novak et al., Murine model for evaluation of protective immunity to influenza virus. *Vaccine* 1993; 11(1):55-60.

Evaluation of Cellular Immune Responses (1) Cytokine ELISA

Spleen or inguinal lymph nodes cells ($0.2×10^6$/200 μl complete RPMI medium) will be prepared from immunized mice at 2 weeks after the last immunization, and stimulated in vitro with inactivated influenza virus at a final concentration of 1 μg/ml in complete RPMI medium. Sha et al., Induction of CD4(+) T-cell-independent immunoglobulin responses by inactivated influenza virus. *J Virol.* 2000; 74(11):4999-5005. Kang et al. Enhancement of mucosal immunization with virus-like particles of simian immunodeficiency virus. *J. Virol.* 2003; 77(6):3615-23. Kang et al. Intranasal immunization with inactivated influenza virus enhances immune responses to coadministered simian-human immunodeficiency virus-like particle antigens. *J. Virol.* 2004; 78(18): 9624-32. After 72 h the cells will be centrifuged and the supernatant will be collected and stored at •80° C. until assayed. Cytokine production (TNF-α, IFN-γ, IL-4, IL-6 and IL-10) will be determined according to the manufacturer's instructions.

(2) ELISPOT Assays

Freshly isolated splenocytes and LN cells ($0.5–1.0×10^6$/200 μl complete RPMI) from immunized mice will be cultured for 36 h in the presence of 1 μg/ml formalin of inactivated influenza virus in complete RPMI medium, as previously described. Kang et al. Intranasal immunization with inactivated influenza virus enhances immune responses to coadministered simian-human immunodeficiency virus-like particle antigens. *J Virol.* 2004; 78(18):9624-32. Briefly, capture antibodies IFN-γ, IL-4, IL-2, IL-5 and IL-12p70 (4 μg/ml in sodium bicarbonate buffer, pH9.6) will be used to coat Multiscreen 96-well filtration plates (Millipore) at 4° C.

overnight. After blocking the antibody-coated plates with 10% fetal bovine serum in RPMI 1640 for 1 h at 37° C., the freshly isolated splenocytes or lymphocytes will be added to each well in complete RPMI buffer 1640, in duplicate wells. Spleen cells ($1.0 \times 10^6/200$ µl) mixed with inactivated influenza virus (1 µg/ml) or peptide stimulants will be cultured for 36-40 h. Similarly, LN cells ($1.0 \times 10^6/200$ µl) will be cultured in the presence of inactivated influenza virus (1 µg/ml). To detect cytokine specific spots, we will use biotinylated anti-mouse antibodies specific to IFN-γ, IL-4, IL-2, IL-5 and IL-12, and streptavidin-HRP (horseradish peroxidase). Spots will be developed with stable diaminobenzidine (Research Genetics) and counted in an ELISPOT reader (Cellular Technology).

Skountzou et al., Transcutaneous immunization with inactivated influenza virus induces protective immune responses, *Vaccine* 24 (2006) 6110-6119.

Example 10

Immunization with Pseudoinfectious Virus

West Nile virus (WNV) is a positive-sense, single-stranded RNA virus belonging to the *Flavivirus* genus of the Flaviviridae family. A pseudoinfectious WNV lacking a functional C gene, named RepliVAX WN, have been developed as a vaccine candidate against West Nile encephalitis. Widman et al., Construction and characterization of a second-generation pseudoinfectious West Nile virus vaccine propagated using a new cultivation system, *Vaccine* (2008) 26, 2762-2771. RepliVAX WN can be safely propagated at high titer in BHK cells and vaccine-certified Vero cells engineered to stably express the C protein needed to trans-complement RepliVAX WN growth. A second-generation RepliVAX WN (RepliVAX WN.2) will be recently developed.

Cell Cultures and Viruses

The baby hamster kidney cells used for all studies and Vero cells used for titration and blind passaging studies have been previously described. Mason et al. Production and characterization of vaccines based on flaviviruses defective in replication. *Virology* 2006; 351(2):432-43. Vaccine-substrate Vero cells (S. Whitehead, NIH, Bethesda, Md.) will be maintained in OptiPro serum-free medium (SFM) (Gibco/Invitrogen, Carlsbad, Calif.). Packaging cell lines will be produced by puromycin (10 µg/ml) selection of cell lines harboring Venezuelan equine encephalitis virus replicons (VEErep) encoding the desired flavivirus genes (see below). The snowy owl isolate of WNV NY99 (R. B. Tesh, UTMB) will be used for all animal studies. Xiao et al. West Nile virus infection in the golden hamster (*Mesocricetus auratus*): a model for West Nile encephalitis. *Emerg Infect Dis* 2001; 7(4):714-21. Mice will be challenged with 1000 ffu of virus (corresponding to 10 LD50 in 8-week-old mice), and hamsters will be challenged with $1 \times 10^6$ ffu.

Antigen

Plasmid constructs, RNA transcription and transfections will be conducted essentially as described in Widman et al., Construction and characterization of a second-generation pseudoinfectious West Nile virus vaccine propagated using a new cultivation system, *Vaccine* (2008) 26, 2762-2771.

RepliVAX WN particles obtained from electroporation of synthetic RepliVAX WN RNA into BHK (VEErep/Pac-Ubi-C*) cells will be used for subsequent infections. RepliVAX WN passaging will be performed at a multiplicity of infection (MOI) of 0.01 in MEM containing 1% FBS, 10 mM HEPES, and antibiotics (maintenance-media). Medium will be replaced at 24 h intervals post-infection, and the 72 h sample will be used for subsequent infections.

RepliVAX WN will be mixed with oxacyclohexadecan-2-one and other suitable components to form a nasal formulation as described above.

Immunization

Groups of fifteen 5-week-old female Swiss Webster mice (Harlan Sprague Dawley, Indianapolis, Ind.) will be immunized intransally with RepliVAX WN, RepliVAX WN.2, or diluent alone (mock). Animals will be monitored for vaccine-induced side effects including lethargy and hind-limb paralysis. At 21 days post-vaccination serum will be collected from all of the animals by retro-orbital bleed. Seven days later animals will be challenged i.p. with 10 LD50 of WNV NY99 and monitored for changes in weight and health for 14 days. Animals scored moribund will be euthanized and scored as "dead" the following day.

Groups of ten 4-week-old female Syrian hamsters (Harlan Sprague Dawley) will be immunized i.p. with RepliVAX WN or diluent (mock) in a volume of 100 µl of maintenance-media. Animals will be monitored for 3 weeks for vaccine-induced side effects, and at day 21 post-vaccination sera will be obtained from all animals. Seven days later, hamsters will be challenged i.p. with $1 \times 10^6$ ffu of WNV NY99 diluted in 100 µl PBS+10% FBS, and weight and health will be monitored for 3 weeks. Animals scored moribund will be euthanized and scored as "dead" the following day.

ELISAs and Neutralization Assays

Serum antibody titers to WNV E and NS1 will be measured using an enzyme-linked immunosorbent assay (ELISA). Immulon 2HB microtiter plates (Thermo Labsystems, Franklin, Mass.) will be sensitized with NS1 or E protein harvested from VEErep-bearing cell lines (see above), and then incubated with individual sera (diluted 1:100) for 1 h. Goat anti-mouse IgG HRP-conjugated antibody (KPL, Gaithersburg, Md.) will be added to the plates for 1 h, and the bound HRP will be detected by incubation with TMB (Sigma), prior to quenching with 1M HCl. The reaction product will be quantitated spectrophotometrically at 450 nm, and values will be corrected for background activity detected from wells that received diluent in place of sera. Neutralizing antibody (neut) titers will be determined by measuring the serum dilution that produced a 90% reduction of luciferase activity from Vero cells infected with a firefly luciferase-encoding WNV VLP (WNVLP), an assay that has been shown to be comparable to classical focus reduction assays. Serial twofold dilutions of heat-inactivated pooled serum samples will be incubated for 1 h at 37° C. with a fixed amount of luciferase-encoding WNVLPs. These VLP/serum mixtures will be used to infect Vero cell monolayers in black 96-well plates (Greiner Bio-One, Monroe, N.C.) for 2 h at which time the infection medium will be replaced with maintenance-media and allowed to incubate for 24 h. A solution containing cell lysis buffer with 25% Steady-Glo luciferase substrate (Promega, Madison, Wis.) will be added to each well in a 1:1 (v/v) ratio to the culture medium. The plates will be read on a luminometer (Applied Biosystems, Foster City, Calif.) and light output will be expressed as the percent activity obtained from lysates prepared from monolayers infected with WNVLPs incubated at 37° C. in diluent only.

Example 11

In vitro Trans-mucosal Permeation of Antibodies

Prolia™ (denosumab) is a human IgG2 monoclonal antibody with affinity and specificity for human RANKL (receptor activator of nuclear factor kappa-B ligand). Prolia binds to RANKL, a transmembrane or soluble protein essential for the formation, function, and survival of osteoclasts, the cells responsible for bone resorption. Prolia prevents RANKL from activating its receptor, RANK, on the surface of osteoclasts and their precursors. Prevention of the RANKL/RANK interaction inhibits osteoclast formation, function, and survival, thereby decreasing bone resorption and increasing bone mass and strength in both cortical and trabecular bone.

Denosumab has an approximate molecular weight of 147 kDa and is produced in genetically engineered mammalian (Chinese hamster ovary) cells. (See, pi.amgen.com/united states/prolia pi.pdf)

Nasal formulation of denosumab will be prepared with oxacyclohexadecan-2-one as described above. An in vitro permeation study will be carried out using excised goat nasal mucosa. Permeation profiles will be evaluated by ELISA. Histological study of nasal mucosae before and after permeation study will be also conducted.

In Vitro Permeation Study

The Franz Cell in vitro Finite Dose Model has offered a reliable method to predict a agent's topical or trans-nasal mucosal delivery and absorption profile in vivo. Briefly, a Franz cell a donor chamber, a membrane, which can be skin or nasal mucosa (human or animal), and a receptor chamber. The test formulation is placed on the membrane, and the appearance of the test agent in the receptor chamber is measured at various time points.

The in vitro permeation study will be conducted using a Franz diffusion cell containing 100 ml of phosphate buffer (pH 6, 0.1M) using an excised goat nasal mucosa. Raney, et al., $30^{th}$ anniversary of the Franz cell finite dose model: the crystal ball of topical drug development. *Drug Delivery Tech.* 2008, 8, 7: 32. Schmidt et al. Validation of excised bovine nasal mucosa as in vitro model to study drug transport and metabolic pathways in nasal epithelium. *J Pharm Sci.* 2000; 89: 396-407. Basu, et al. *Sci Pharm.* 2009; 77: 899-910. The goat nose will be obtained from local slaughterhouse. After removing the skin, the nose will be stored on ice cold phosphate buffer (pH 7.4, 0.05 M). The septum will be fully exposed and nasal mucosa will be carefully removed using forceps and surgical scissors. The mucosal tissues will be immediately immersed in Ringer's solution. The nasal mucosa will be mounted on the Franz diffusion cell displaying permeation area of about 2 to 3 $cm^2$ and nasal formulation containing denosumab will be placed on it. Throughout the study the buffer solution in the chamber will be maintained at 37±1° C. by connecting the Franz diffusion cell with water bath. At predetermined time intervals 1 ml of the samples will be withdrawn at a time, and an equal amount of phosphate buffer will be replaced.

ELISA 96-well plates (Nunc) will be coated with RANKL in 0.05 mol/L carbonate coating buffer (pH 9.6) at 4° C. overnight. Plates will be blocked using bovine serum albumin. Samples from the Franz diffusion cell receptor chamber will be serially diluted in duplicate across the plate in blocking buffer and incubated for 1 h at 37° C. After washings, plates will be incubated with horseradish peroxidase (HRP)-conjugated IgG (Southern Biotechnology). After washings, plates will be developed for 30 min at room temperature with tetramethylbenzidine substrate (Sigma) and the reaction stopped; optical densities will be read at 450 nm.

Histological Evaluation of Nasal Mucosa

Histological study of excised nasal mucosa will be conducted after 5 h in vitro permeation to detect if any significant histological change has occurred during the experiment. After permeation study nasal mucosa will be cleared off the formulation, sectioned with a rotary microtome and fixed in 10% formalin solution. The sectioned tissue will be then stained with hematoxylin and eosin. Another normal mucosa will be taken as a control and treated similarly. Tissue sections will be observed under optical microscope.

The embodiments illustrated and discussed in this specification are intended only to teach those skilled in the art the best way known to the inventors to make and use the invention. Nothing in this specification should be considered as limiting the scope of the present invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

All patents, applications, publications, test methods, literature, and other materials cited herein are hereby incorporated by reference.

What is claimed is:

1. A pharmaceutical composition for nasal immunization comprising:

a macrocyclic permeation enhancer, a liquid carrier, an emulsifying agent, and a therapeutically effective amount of an antigen; wherein said macrocyclic permeation enhancer is a Hsieh enhancer having the following structure:

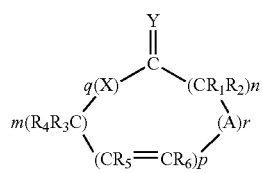

wherein X is oxygen, sulfur or an imino group of the structure

wherein Y is oxygen, sulfur or an imino group of the structure
=N—R with the proviso that when Y is the imino group, X is an imino group, and when Y is sulfur, X is sulfur or an imino group, A is a group having the structure

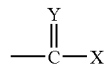

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, wherein the antigen is selected from the group consisting of an Anthrax protective antigen, a carbohydrate, and DNA.

2. The composition of claim 1, wherein said Hsieh enhancer is selected from the group consisting of 3-methylcyclopentadecanone, 9-cycloheptadecen-1-one, cyclohexadecanone, cyclopentadecanone, oxacyclohexadecan-2-one and mixtures thereof.

3. The composition of claim 1, further comprising a crystallization inhibitor.

4. The composition of claim 1, further comprising an enzyme inhibitor.

5. The composition of claim 4, wherein said enzyme inhibitor is selected from the group consisting of leupeptin and aprotinin.

6. A method of immunizing a mammal comprising the steps of:

formulating a composition comprising: a macrocyclic permeation enhancer, a liquid carrier, an emulsifying agent, and a therapeutically effective amount of an antigen; wherein said macrocyclic permeation enhancer is a Hsieh enhancer having the following structure:

wherein X is oxygen, sulfur or an imino group of the structure wherein Y is oxygen, sulfur or an imino group of the structure =N—R with the proviso that when Y is the imino group, X is an imino group, and when Y is sulfur, X is sulfur or an imino group, A is a group having the structure wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, wherein the antigen is selected from the group consisting of an Anthrax protective antigen, a carbohydrate, and DNA; and, administering the composition to the mammal by nasal administration.

7. The method of claim 6, wherein said Hsieh enhancer is selected from the group consisting of 3-methylcyclopentadecanone, 9-cycloheptadecen-1-one, cyclohexadecanone, cyclopentadecanone, oxacyclohexadecan-2-one and mixtures thereof.

8. The method of claim 6, further comprising a crystallization inhibitor.

9. The method of claim 6, further comprising an enzyme inhibitor.

10. The method of claim 9, wherein said enzyme inhibitor is selected from the group consisting of leupeptin and aprotinin.

11. A pharmaceutical composition for nasal immunization comprising: a macrocyclic permeation enhancer, a liquid carrier, an emulsifying agent, and a therapeutically effective amount of an antibody; wherein said macrocyclic permeation enhancer is a Hsieh enhancer.

* * * * *